United States Patent [19]
Snell

[11] Patent Number: 5,518,001
[45] Date of Patent: May 21, 1996

[54] CARDIAC DEVICE WITH PATIENT-TRIGGERED STORAGE OF PHYSIOLOGICAL SENSOR DATA

[75] Inventor: Jeffery D. Snell, Northridge, Calif.

[73] Assignee: Pacesetter, Inc., Sylmar, Calif.

[21] Appl. No.: 261,562

[22] Filed: Jun. 17, 1994

[51] Int. Cl.$^6$ .................................. A61B 5/0432
[52] U.S. Cl. ............................ 128/697; 607/27
[58] Field of Search .................... 128/697; 607/27

[56] References Cited

U.S. PATENT DOCUMENTS

| | | | |
|---|---|---|---|
| 3,782,367 | 1/1974 | Hochberg et al. | 128/2.06 A |
| 3,898,984 | 8/1975 | Mandel et al. | 128/2.1 A |
| 4,019,518 | 4/1977 | Maurer et al. | 128/419 R |
| 4,142,533 | 3/1979 | Brownlee et al. | 128/419 PT |
| 4,193,393 | 3/1980 | Schlager | 128/710 |
| 4,203,447 | 5/1980 | Keller, Jr. et al. | 607/31 |
| 4,267,843 | 5/1981 | McDonald et al. | 607/31 |
| 4,281,664 | 8/1981 | Duggan | 128/696 |
| 4,374,382 | 2/1983 | Markowtiz | 128/419 P |
| 4,596,255 | 6/1986 | Snell et al. | 128/697 |
| 4,625,730 | 12/1986 | Fountain et al. | 128/419 D |
| 4,681,111 | 7/1987 | Silvian | 128/697 |
| 4,791,936 | 12/1988 | Snell et al. | 128/697 |
| 4,825,869 | 5/1989 | Sasmor et al. | 128/419 PT |
| 5,193,550 | 3/1993 | Duffin | 128/697 |
| 5,312,446 | 5/1994 | Holschbach et al. | 607/9 |
| 5,330,513 | 7/1994 | Nichols et al. | 607/32 |

*Primary Examiner*—William E. Kamm
*Attorney, Agent, or Firm*—Malcolm J. Romano; Harold C. Schloss

[57] ABSTRACT

A cardiac device that stores physiological sensor data from multiple sensors is provided. A patient may use a portable triggering device to cause the cardiac device to store the data when the patient experiences symptoms that appear to be due to an abnormal heart condition. Alternatively, the data may be stored when the cardiac device identifies an abnormal physiological condition. A physician may select which sensors are used to store the data and may also adjust the number of memory buffers in which the data is to be stored.

26 Claims, 2 Drawing Sheets

5,518,001

CARDIAC DEVICE WITH PATIENT-TRIGGERED STORAGE OF PHYSIOLOGICAL SENSOR DATA

BACKGROUND OF THE INVENTION

This invention relates to implantable medical devices, and particularly to implantable cardiac devices that are capable of storing physiological data.

Patients who have heart abnormalities often benefit from the surgical implantation of a cardiac device, such as a pacemaker or a cardioverter/defibrillator. For example, if a patient suffers from bradycardia, a condition in which a patient's heart beats too slowly, a cardiac stimulating device can be used to provide pacing pulses to the patient's heart. Other patients suffer from heart arrhythmias such as tachycardia, in which the heart beats too quickly. Many implantable cardiac stimulating devices have cardiac sensors that may be used to monitor a patient's internal cardiac signals to detect and terminate cardiac abnormalities, such as episodes of tachycardia.

Cardiac stimulating devices may also provide stimulating pulses to a patient's heart based on the patient's measured level of physical activity. Such cardiac stimulating devices, known as rate-responsive pacemakers, determine the physiological needs of the patient by monitoring the patient's physical movements using activity sensors. Various other sensors may also be used by cardiac devices either to determine the appropriate stimulating pulses to deliver to the patient's heart or to monitor the patient's condition in more detail. For example, sensors may be used to measure the patient's blood flow rate, blood oxygen level, or cardiac wall motion. Additional sensors may be used to measure the patient's internal temperature or respiration rate. Each of these sensors generates data that may be used by a cardiac stimulating device to determine the number and intensity of stimulating pulses that should be provided, or by a cardiac monitoring device to monitor a patient's physical condition.

Because cardiac stimulating devices can generally be programmed to perform various functions in response to the data measured by the various physiological sensors, the response of cardiac stimulating devices to measured cardiac signals and other physiological data can be tailored by a physician to suit the needs of individual patients. Without individually tailoring the device settings, some patients may experience discomfort if they suffer from an abnormal cardiac condition that is not detected and treated adequately by the cardiac stimulating device.

In order to determine whether a cardiac stimulating device is programmed properly, a physician can direct the device to store measured cardiac signals in memory. These signals can then be transmitted from the cardiac device to an external display device, for review by the physician. However, it would also be desirable if a cardiac stimulating device or cardiac monitoring device could be directed to store data from sensors such as a blood flow sensor, a blood oxygen level sensor, an activity sensor, a temperature sensor, a respiration rate sensor, or other physiological sensors, because data from these sensors may also affect the response of the cardiac stimulating device and may be useful for accurately diagnosing a patient's condition.

Because the memory that is available in a cardiac stimulating device or cardiac monitoring device is limited, it would be desirable to be able to direct a cardiac stimulating device to store sensor data from only certain selected sensors to conserve memory. Preferably, the physician can use an external control device to program the cardiac stimulating device or monitoring device to store data from the selected sensors. Further, it would be desirable for the patient to be able to direct the device to retain data during an episode of cardiac discomfort. Such data would be valuable to the physician for diagnosing the patient's condition and for adjusting the settings of the cardiac stimulating device to prevent further discomfort. If desired, data could also be retained automatically, when the cardiac stimulating or monitoring device determines that an abnormal physiological condition exists.

SUMMARY OF THE INVENTION

Therefore, in accordance with the present invention, a cardiac device is provided that has multiple sensors for measuring various physiological parameters, such as a blood flow sensor, a blood oxygen level sensor, an activity sensor, a temperature sensor, a respiration rate sensor, or a cardiac wall motion sensor. A physician can direct the cardiac stimulating device to store data from some or all of the sensors. Data that is measured by the sensors is stored in memory within the cardiac device. The data may be retained either automatically, (e.g., when an abnormal cardiac event such as an arrhythmia is detected), or when the cardiac device is signalled by a patient.

The patient may direct the cardiac device to retain sensor data by telemetering a trigger signal to the device using a dedicated triggering device. The triggering device is battery powered and portable. Preferably the triggering device is small and lightweight, so that it may be carried by the patient. The triggering device contains a conventional telemetry head that allows the patient to communicate with the cardiac device using standard telemetry techniques. Alternatively, the patient may use a triggering device such as a magnet to activate a reed switch within the cardiac device.

The cardiac device preferably stores data in memory continuously, so that data will be stored prior to the time at which the patient signals the cardiac device with the triggering device. If desired, the data may be stored in memory in the form of one or more circular buffers. Preferably, the physician can select the number of buffers that are used and the length of time that the cardiac stimulating device is to store data after the trigger signal is received.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 4 is a schematic diagram showing how a portion of the memory can be organized in the form of multiple circular buffers.

DETAILED DESCRIPTION OF THE PREFERRED EMBODIMENTS

Figure 1:
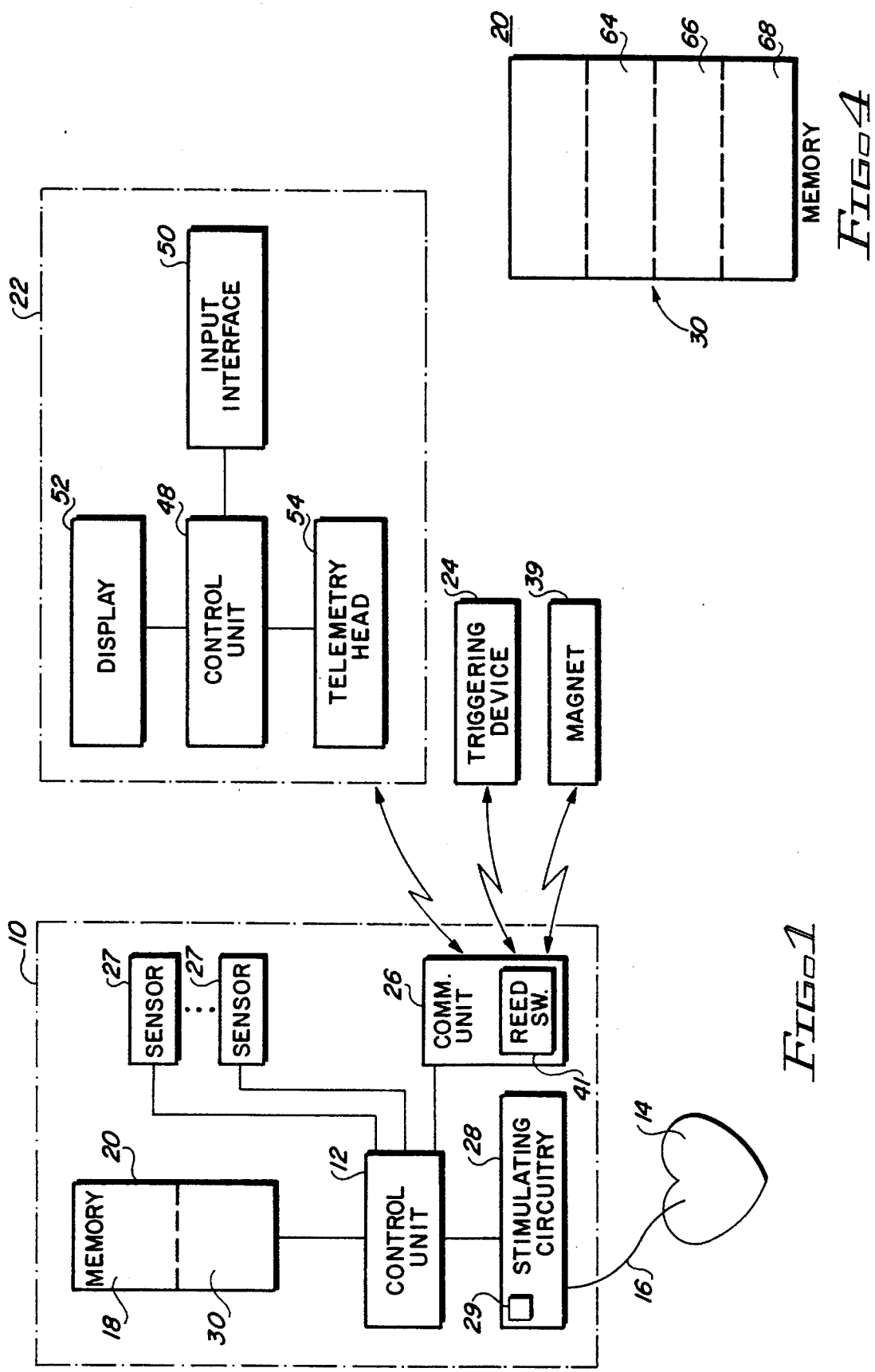
FIG. 1 is a schematic diagram of a system including a cardiac device in accordance with the present invention.

A cardiac device 10 in accordance with the present invention is shown in FIG. 1. Preferably, the cardiac device 10 has a control unit 12, which contains a microprocessor (not shown) and control circuitry (not shown). The cardiac device 10 may contain circuitry 28 for stimulating a patient's heart 14, so that the control unit 12 can cause pacing pulses, antitachycardia pulses, or a defibrillating shock to be applied to the patient's heart 14 via a lead 16. If desired, the cardiac device 10 can perform solely monitoring functions. Whether the cardiac device 10 is a cardiac stimulating device or only a cardiac monitoring device, the cardiac device 10 communicates with a programmer 22 and a triggering device 24 via well-known radio frequency telemetry techniques. Signals may be sent and received by the cardiac device 10 in a conventional manner using a communication unit 26.

In operation, the control unit 12 executes instructions stored in a memory region 18 of a memory 20, in order to monitor the patient's condition or to provide stimulation pulses to the patient's heart. The control unit 12 analyzes data from sensors 27, which may include a blood flow sensor, a blood oxygen level sensor, an activity sensor, a temperature sensor, a respiration rate sensor, a cardiac wall motion sensor and other physiological sensors. The control unit 12 also analyzes the patient's heartbeat signals in a conventional manner using a sensor 29, which is contained within the stimulating circuitry 28. For example, if one of the sensors 27 measures the patient's activity level, the control unit 12 can cause stimulating pulses to be applied to the patient's heart more rapidly when the patient is active than when the patient is inactive to accommodate the patient's physiological needs. Schulman U.S. Pat. No. 4,232,679 and Fountain et al. U.S. Pat. No. 4,625,730 describe previously known telemetry techniques and techniques for programming cardiac devices and storing sensor data.

The sensor 29 may have multiple inputs to measure signals from various regions of the patient's heart. Cardiac data measured by the sensor 29 is passed to the control unit 12 in order to identify cardiac signals such as R-waves. When an R-wave is sensed, interface circuitry contained in the control unit 12, generates interrupt signals indicating that a cardiac event has been detected. The interface circuitry also generates event marker codes (such as the letter "R" for R-wave) that correspond to the detected event. The control unit 12 stores data from the sensors 27 and the sensor 29 in the memory 20. Either sampled data or processed data such as the event markers may be stored.

Preferably, the control unit 12 contains a real-time clock, so that the time at which data is measured by the sensors 27 and 29 (step 206 in FIG. 5) can be accurately recorded. Because the time at which each heartbeat occurs is known, the control unit 12 can calculate the time interval that elapses between successive beats, and can store these intervals sequentially in a memory region 30 of the memory 20. If desired, a digitized version of the full measured intracardiac electrogram could be stored, rather than the beat-to-beat interval length, provided that the cardiac device 10 has a sufficient memory capacity.

The data from the sensors 27 is preferably stored sequentially in the memory region 30 of the memory 20. In order to reduce the amount of memory that is required to store the data from the sensors 27 and 29, the instructions that control the operation of the control unit 12 can be selectively programmed by the physician to direct the control unit to store data from a subset of the sensors 27 and 29 (step 204 in FIG. 5).

The sensor data that is recorded in the memory region 30 of the memory 20 is preferably stored in the order in which it is measured, beginning at an initial predetermined memory address. Because the memory 20 is finite, when new sensor data is stored in the memory 20 the control unit 12 must replace old sensor data. In order to track the time at which data is measured, the value of the real-time clock is stored in the memory region 30 each time it becomes necessary to begin replacing data at the initial memory address.

Figure 2:
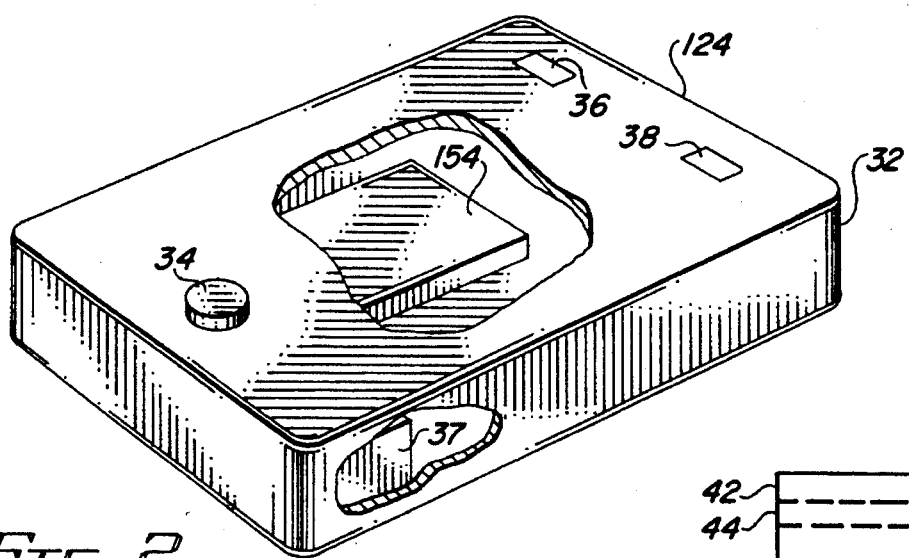
FIG. 2 is a perspective view, partially in section, of a triggering device in accordance with the invention.

When a patient experiences what appear to be the symptoms of an abnormal cardiac event such as an arrhythmia, the patient can use the triggering device 24 to send a trigger signal to the cardiac device 10. A triggering device 124 is shown in more detail in FIG. 2. The triggering device 124 has a body 32 (FIG. 2) and a button 34 (FIG. 2). A conventional telemetry head 154 (FIG. 2), is contained within the triggering device 124 to allow communication with the cardiac device 10 (FIG. 1) via telemetry. The patient may press the button 34 while holding the triggering device in the proximity of the implanted cardiac device 10 (FIG. 1) in order to telemeter the trigger signal to the communication unit 26 in the cardiac device 10 (FIG. 1) (step 208 in FIG. 5). The triggering device 124 has a power indicator 36 (FIG. 2), which is lit when the triggering device 124 has sufficient power available for operation. The triggering device 124 is preferably powered by a battery (FIG. 2), and is portable.

The triggering device 124 also has a confirmation indicator 38 (FIG. 2). When the trigger signal is successfully received by the communication unit 26 (FIG. 1) (step 210 in FIG. 5), a confirmation signal may be transmitted by the communication unit 26 to the triggering device 124. Upon receiving the confirmation signal, the confirmation indicator 38 emits a beeping tone. Alternatively, the triggering device 124 may be provided with a visual confirmation indicator that lights up to confirm successful communication with the cardiac device 10 (FIG. 1). Although using a triggering device with a telemetry head allows the patient to confirm when the trigger signal has been received by the cardiac device 10 (FIG. 1), a low-cost alternative is to use a magnet 39 (FIG. 1) to activate a reed switch 41 (FIG. 1) contained within the communication unit in the cardiac device to initiate sensor data storage.

Figure 5:
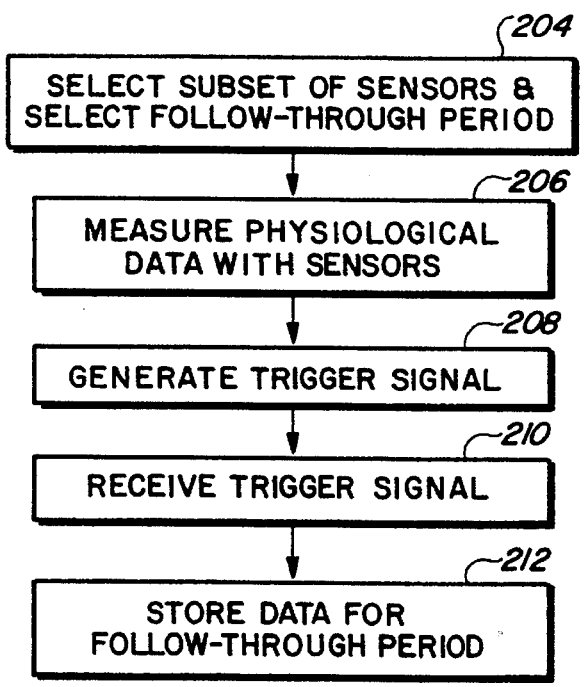
FIG. 5 is a flowchart of the various steps used in storing the physiological data.

Returning to FIG. 1, when the cardiac device 10 receives the trigger signal (step 210 in FIG. 5), the control unit 12 may continue to replace the oldest sensor data with the most recent data for a predetermined period of time (step 212 in FIG. 5). At the end of this period, the control unit 12 continues to provide control of the operation of the cardiac device 10, but does not store additional data. A physician can retrieve the data later to aid in determining the cause of the patient's symptoms.

Figure 3:
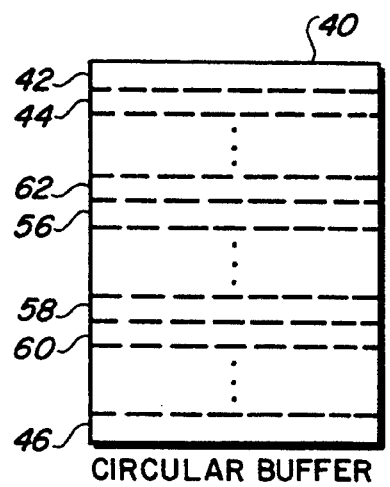
FIG. 3 is a schematic diagram showing memory address locations in a portion of the memory in the cardiac device.

As shown in FIG. 3, the memory region 30 may be organized in the form of a circular buffer 40. The first sensor data is stored at an initial memory address 42, the second is stored at address 44, and so forth, until data is stored in memory address 46. Subsequent data are written over the previously stored data at the addresses 42, 44, and so on, until the memory address 46 is reached, at which point the cycle is once again continued by wrapping around to the memory address 42. Although data are recorded into the circular buffer 40 continuously, the amount of data that can be stored is limited by the buffer size. For example, a memory capacity of approximately 4 kilobytes is sufficient to store the data generated in approximately one hour at a normal level of patient activity. If data are stored less frequently, a longer, although less detailed, recording may be made.

Because the storage capacity of the memory region 30 (FIG. 1) is limited, any new data that are stored results in the loss of previously stored data. However, the physician can adjust the length of time that the device continues to record after the decision to save the data is made. Referring again to FIG. 1, the physician can adjust the value of this follow-through period using the programmer 22. The programmer 22 (see also step 204 in FIG. 5) has a control unit 48 that receives commands entered through an input interface 50, such as a keyboard. The control unit 48 displays the entered commands on a display 52 and sends corresponding control signals to the cardiac device 10 using a telemetry head 54.

If the physician wishes to extend the length of the follow-through period (albeit at the expense of earlier recorded data), the value of the longer follow-through period is sent to the cardiac device 10 by the programmer 22. Alternatively, if the physician wishes to retain data corresponding to measurements taken well before the decision to save the data was made, a shorter follow-through period may be chosen. For example, referring again to FIG. 3, if data is being stored at the memory address 56 when the decision to save the data is made, data will be stored only through the memory address 58, provided that the follow-through period is short. The data in the circular buffer 40 at the memory addresses 60 through 46, and at the memory addresses 42 through 62 represents earlier cardiac activity. At one extreme, all the old data in the memory region 30 can be replaced with new data during the period following the time at which the trigger signal is received, if the follow-though period is made as long as possible. At the other extreme, the follow-through period of time can be effectively eliminated, so that the only old data are retained in the memory region 30 (i.e., data that were stored prior to the time when the trigger signal is received) (see also step 212 of FIG. 5).

Returning now to FIG. 1, if desired, the decision to retain the data may be made automatically by the cardiac device, for example, when certain cardiac events occur, such as when the patient's heart 14 fibrillates. After detecting data corresponding to a fibrillation event, the microprocessor within the control unit 12 continues to store data in the memory 20 until the follow-through period has expired.

Preferably, the physician can selectively limit the number of sensors 27 and 29 from which data are stored in the memory to a subset of the total number available by highlighting corresponding icons on the display 52 or by entering the name of the sensors 27 and 29 to be selected via the input interface 50 (step 204 in FIG. 5). By not storing data from all of the sensors 27 and 29, more of the memory region 30 becomes available for data storage for the sensors 27 and 29 from which data are stored.

A physician can also use the programmer 22 to instruct the cardiac device 10 to retain data in the memory region 30 on demand, at any time. For example, if the physician desires to examine sensor data obtained under normal conditions, the patient may be instructed to walk about slowly for several minutes, following which the physician can use the programmer 22 to direct the cardiac device 10 to retain sensor data.

If the cardiac device 10 supports an auto-trigger mode, in which the cardiac device 10 retains sensor data automatically, without receiving a trigger signal from a patient, the auto-trigger mode may be periodically inhibited to avoid inadvertently losing previously stored data by storing auto-triggered data in place of the data previously stored. Similarly, in order to prevent the loss of either patient-triggered or auto-triggered data, a physician may be warned by the programmer 22 that the memory region 30 contains data that has not been retrieved, before allowing the physician to direct the cardiac device 10 to store new data. Alternatively, the memory region 30 of memory 20 can be organized in the form of separate circular buffers, for example, a buffer 64 dedicated to patient-triggered storage, a buffer 66 dedicated to auto-triggered storage, and a buffer 68 dedicated to the storage of data on demand, as shown in FIG. 4. If three buffers are used, it is not necessary to inhibit any of the modes, because the storage of data in one buffer will not affect the data in the other buffers.

Thus, a cardiac device that stores physiological sensor data from multiple sensors is provided. A patient may use a portable triggering device to cause the cardiac device to store the data when the patient experiences symptoms that appear to be due to an abnormal heart condition. Alternatively, the data may be stored when the cardiac device identifies an abnormal physiological condition. A physician may select which sensors are used to store the data and may also adjust the number of memory buffers in which the data are to be stored. It will be understood that the foregoing is merely illustrative of the principles of this invention, and that various modifications can be made by those skilled in the art without departing from the scope and spirit of the invention.

What is claimed is:

1. An implantable cardiac device for receiving a trigger signal from a triggering device that is operable by a patient when the patient desires to retain physiological data, comprising:

a plurality of sensors for measuring the physiological data;

memory in which to store the data that are measured by the sensors;

memory region means for forming at least one circular buffer in the memory;

control means for storing the data in the memory; and means for receiving the trigger signal from the triggering device when the patient desires to retain the data.

2. The cardiac device defined in claim 1, further comprising:

means for producing a follow-through period signal that represents a follow-through period of time;

means for storing data in the memory during the follow-through period of time when the trigger signal is received by the means for receiving; and means for adjusting the follow-through period to a value ranging from a maximum extent of time to a minimum extent of time; and means for replacing the data in the memory that are old with data that are new during the follow-through period.

3. The cardiac device defined in claim 1 further comprising:

means for detecting when a predetermined cardiac condition occurs; and means for automatically retaining the data in the memory when the predetermined cardiac condition is detected by the means for detecting.

4. The cardiac device defined in claim 3 further comprising:

first circular buffer means for storing patient-triggered data; and second circular buffer means for automatically storing data when the predetermined cardiac condition is detected by the means for detecting.

5. The cardiac device defined in claim 1, wherein the triggering device comprises a portable triggering device.

6. The cardiac device defined in claim 1, wherein the means for receiving the trigger signal comprises a reed switch coupled to the control means.

7. The cardiac device defined in claim 1, further comprising:

means for generating a stimulating pulse; and means for applying the stimulating pulse to a patient's heart.

8. An implantable cardiac device for receiving a trigger signal from a triggering device that is operable by a patient when the patient desires to retain physiological data, comprising:

a plurality of sensors for measuring the physiological data;

memory in which to store the data that are measured by the sensors;

control means for storing the data in the memory; and means for receiving the trigger signal from the triggering device when the patient desires to retain the data, wherein the control means comprises programmable means for receiving programming instructions from a physician that direct the control means to store data from a subset of the sensors.

9. A method for storing data in a cardiac device having a control unit, a plurality of sensors connected to the control unit for sensing physiological data, memory connected to the control unit for storing the physiological data, the memory containing a memory region that is organized as at least one circular buffer, and communications circuitry connected to the control unit for receiving signals generated by a triggering device operable by a patient, the method comprising the steps of:

measuring physiological data with the plurality of sensors;

storing the physiological data in the memory, wherein the step of storing data further comprises the step of storing data in the memory region that is organized as the at least one circular buffer;

generating a trigger signal with the triggering device; and receiving the trigger signal with the communications circuitry when the patient desires to retain the data.

10. The method defined in claim 9, wherein the triggering device further comprises a switch, the method further comprising the steps of:

manually activating the switch; and telemetering the trigger signal to the cardiac device in response to the activation of the switch.

11. The method defined in claim 9, wherein the cardiac device contains stimulating circuitry for applying stimulating pulses to the patient's heart, the method further comprising the step of stimulating the heart with the stimulating circuitry.

12. The method defined in claim 9, wherein the triggering device further comprises a battery, the method further comprising the step of powering the triggering device with the battery.

13. The method defined in claim 9, wherein the triggering device further comprises a power indicator, the method further comprising the step of indicating that power is available to the triggering device with the power indicator.

14. The method defined in claim 9, further comprising the step of confirming that the cardiac device has received the trigger signal.

15. The method defined in claim 10, further comprising the steps of:

detecting a predetermined condition; and automatically retaining data when the predetermined cardiac condition is detected.

16. The method defined in claim 9, wherein the communications circuitry further comprises a reed switch for receiving magnetic trigger signals, the method further comprising the step of triggering the cardiac device with a magnet that produces such magnetic trigger signals.

17. The method defined in claim 9, wherein the memory contains information defining a follow-through period of time, and wherein the step of storing the data in the memory comprises the step of storing the data in the memory for the follow-through period of time after the trigger signal is received, such that data in the memory that are old are replaced with data that are new.

18. The method defined in claim 9, wherein the follow-through period has a value ranging from a maximum extent of time to a minimum extent of time.

19. A method for storing data in a cardiac device having a control unit, a plurality of sensors connected to the control unit for sensing physiological data, memory connected to the control unit for storing the physiological data, the memory containing a memory region that is organized as at least one circular buffer, and communications circuitry connected to the control unit fop receiving signals generated by a triggering device operable by a patient, the method comprising the steps of:

measuring physiological data with the plurality of sensors;

storing the physiological data in the memory, wherein the step of storing data further comprises the step of storing data in the memory region that is organized as the at least one circular buffer;

generating a trigger signal with the triggering device;

receiving the trigger signal with the communications circuitry when the patient desires to retain the data; and selecting a subset of the sensors from which data are to be retained.

20. An implantable cardiac device for receiving a trigger signal from a triggering device that is operable by a patient when the patient desires to retain physiological data, the implantable cardiac device comprising:

a plurality of sensors for measuring the physiological data;

memory in which to store the data that are measured by the sensors;

memory region means for forming at least one circular buffer;

control means for storing the data in the memory; and means for receiving the trigger signal from the triggering device when the patient desires to retain the data, wherein the data are retained by the memory when the trigger signal is received by the means for receiving, wherein the control means can be programmed to store data in the memory from a subset of the sensors.

21. The cardiac device defined in claim 20 further comprising means for storing the data from the sensors in the memory for a follow-through period of time after the trigger signal is received by the means for receiving.

22. The cardiac device defined in claim 21 further comprising:
   means for producing a follow-through period signal that represents the follow-through period of time; and
   means for adjusting the follow-through period of time to a value ranging from a maximum extent of time to a minimum extent of time.

23. The cardiac device defined in claim 20, further comprising means for automatically retaining data when a predetermined cardiac condition is detected.

24. The cardiac device defined in claim 20, wherein the means for receiving the trigger signal comprises a reed switch coupled to the control means.

25. The cardiac device defined in claim 20, wherein the cardiac device comprises:
   means for generating a stimulating pulse; and
   means for applying the stimulating pulse to a patient's heart.

26. The apparatus defined in claim 20 further comprising:
   first circular buffer means for storing patient-triggered data; and
   second circular buffer means for automatically storing data.

* * * * *